United States Patent [19]

Levy

[11] Patent Number: 4,640,266

[45] Date of Patent: Feb. 3, 1987

[54] SENSORY STIMULATION ENCLOSURE

[76] Inventor: Zubin Levy, 4718 Reeves Rd., Ojai, Calif. 93023

[21] Appl. No.: 645,193

[22] Filed: Aug. 29, 1984

[51] Int. Cl.[4] ............................................. A61B 19/00
[52] U.S. Cl. ..................... 128/1 R; 128/25 A; 128/1 C; 272/2; 272/8 M
[58] Field of Search ............ 128/1 R, 1 C, 630, 25 A; 272/2, 8 M

[56] References Cited

U.S. PATENT DOCUMENTS

| | | |
|---|---|---|
| 652,516 | 6/1900 | Kotin . |
| 1,223,488 | 4/1917 | Goldstein . |
| 3,014,477 | 12/1961 | Carlin ................................. 128/1 C |
| 3,184,872 | 5/1965 | Way ................................ 40/106.53 |
| 3,643,941 | 2/1972 | Kashar ............................... 128/1 C |
| 3,660,952 | 5/1972 | Wilson ................................. 52/81 |
| 3,826,250 | 7/1974 | Adams ................................... 272/2 |
| 4,205,521 | 6/1980 | Cazanas ............................ 272/8 M |

FOREIGN PATENT DOCUMENTS 3237147  4/1984  Fed. Rep. of Germany .......... 272/2

Primary Examiner—Kyle L. Howell
Assistant Examiner—Ruth S. Smith
Attorney, Agent, or Firm—Dowell & Dowell

[57] ABSTRACT

A sensory stimulation and entertainment enclosure or chamber having light reflective inner surfaces wherein one or more people may be seated and wherein an integration of an occupant's senses is achieved through the use of optical lighting systems, multi-reflective imagery, multi-directional sound systems, controlled ventilation systems, and olfactory stimuli so as to thereby relieve stress while simultaneously entertaining the occupants.

17 Claims, 10 Drawing Figures

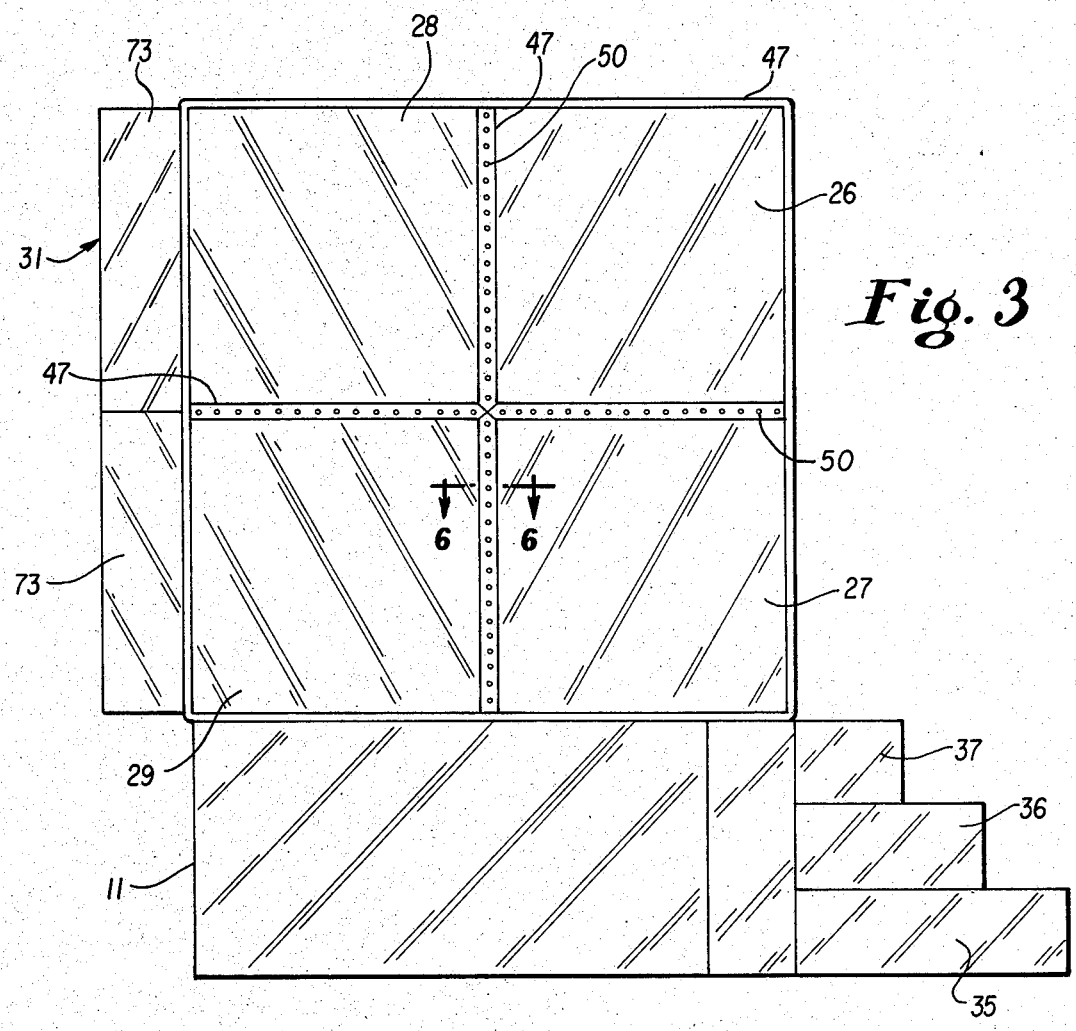
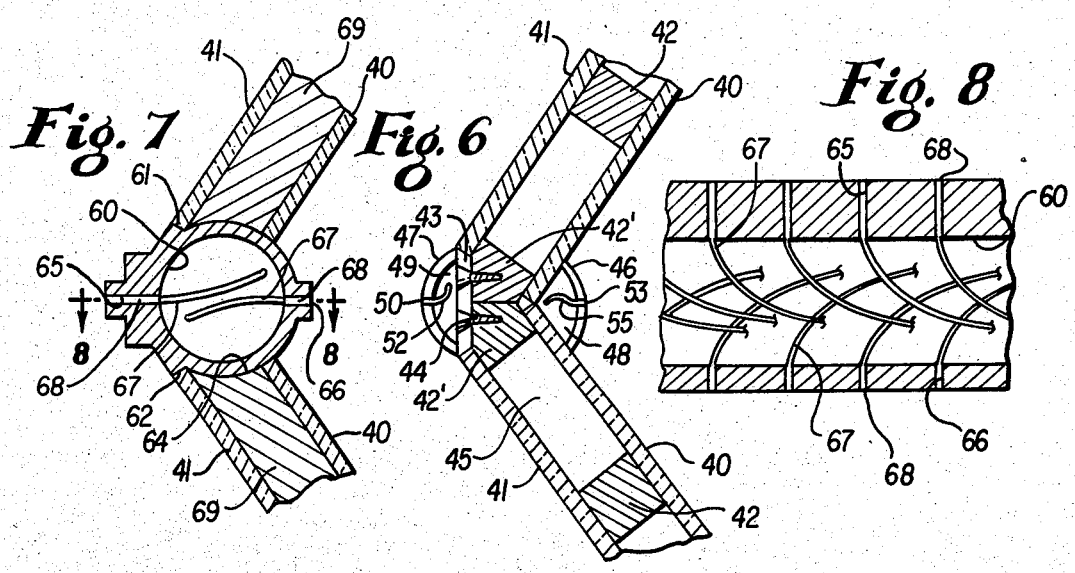

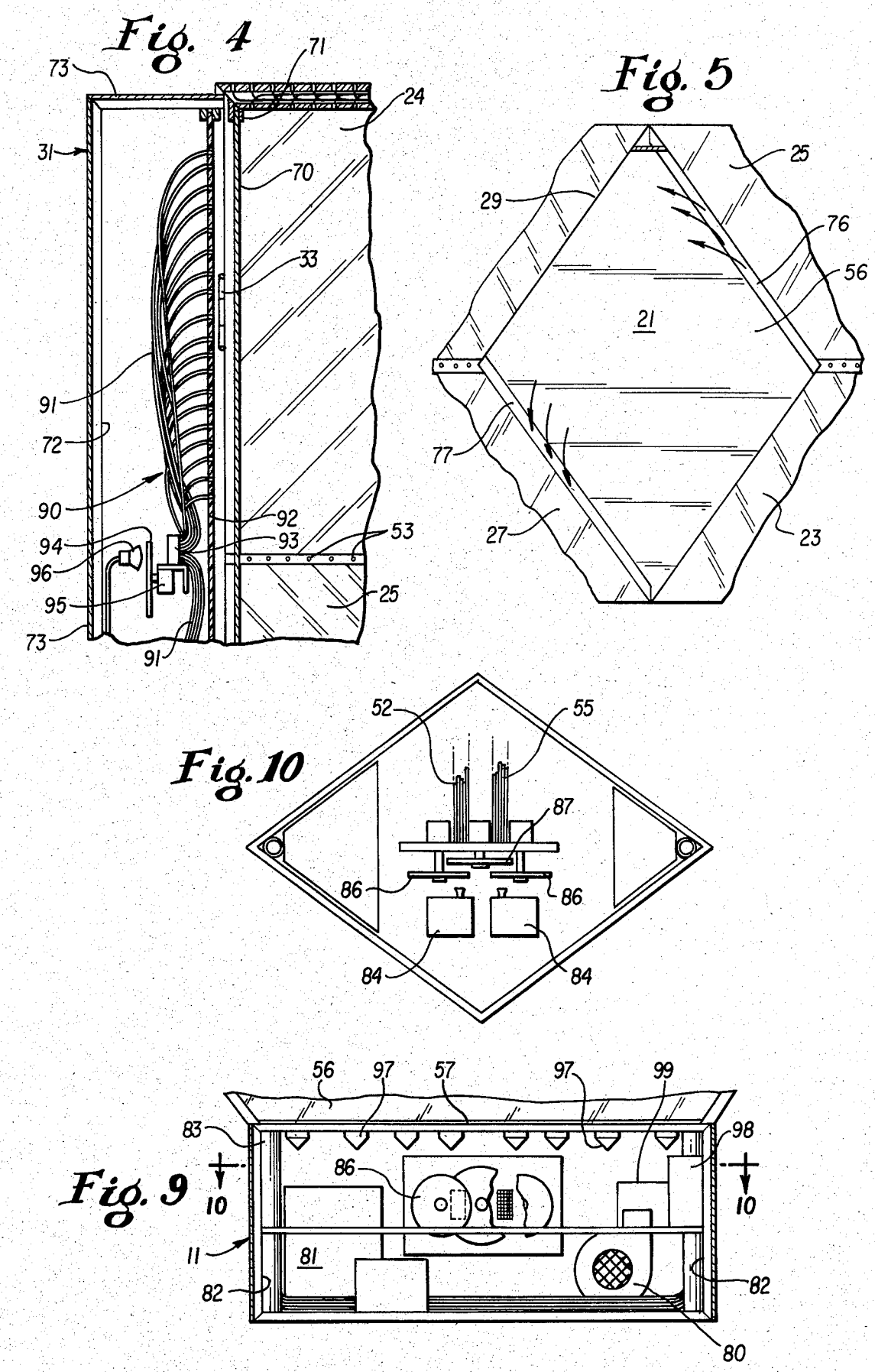

SENSORY STIMULATION ENCLOSURE

BACKGROUND OF THE INVENTION

1. Field of the Invention

This invention is generally related to devices for stimulating an individual's senses and more specifically to an enclosure having a controlled atmosphere and which is substantially constructed of mirrored surfaces so that a person within the enclosure may be entertained and experience a plurality of selective multi-reflected visual displays of changing imagery which are combined with audio, olfactory, and other stimuli to an extent that the occupant is both mentally and physically relaxed and refreshed through a process of stimulating and integrating the senses so that substantially, all thought processes are focussed on the present activity within the enclosure.

2. History of the Invention

As the day-to-day activities of life become increasingly more pressured, exacting, competitive and hurried, the mental and physical stresses upon people are multiplied significantly. In order to continue to cope with the build up of stress, people must find ways to release their anxieties and find relaxation. Relaxation, however, not only must be of the physical type, but, to be complete, must also permit mental stress relief.

In today's quickly changing and fast-paced world, too many people are not able to remove themselves from their hurried routines and find their only break in only different forms of stressful endeavor. Often in an attempt to obtain release from stress, a person may directly channel their activity into simply a different type or form of stressful situation. For example, people who look to release tension through physical exercise will frequently only add to their overall mental stress as the competition of the activity becomes so mind consuming or controlling that there results an increase in emotional output which increases personal anxiety levels. Conversely, even passive activities which are considered by many to be both physically and emotionally peaceful and relaxing may often create additional stress. This stress may result from the mental involvement in games where players are pitted against other players; from fright or distress induced through distressing media; mental involvement in sports competition; and personal or emotional involvement in the story line of movies, shows and the like.

In an effort to find other releases to the build up of mental and physical stresses, some people look to totally removing themselves from the fast paced involvement of daily duties and other activities. They look to remote locations such as special resorts or secluded mountain hideways where there is time to relax and peaceful surroundings. Many people, however, cannot afford the time nor the expenses involved in spending time at remote retreats.

Others have sought various forms of controlled physical exercise in an effort to find an escape from stress. Health spas cater not only to the physical exercise but provide hot tubs and saunas and the like to relieve tensions and ease muscles. Again, such establishments are not always available to a wide section of society, and, further, because of the routines which must be followed and the social atmosphere which tends to exist, the overall environment may not be conducive to individual rest and relaxation.

Some innovations have also been developed to deal with the release of built-up stress and anxiety. In U.S. Pat. No. 3,826,250 to Adams, a sensory stimulation apparatus is disclosed. In this apparatus a person may be seated in a rockable container wherein various sensory stimuli are provided. The device, however, is operable by the person within the enclosure and, therefore, conscious decisions and specific physical motor controlled movements must be made during the use of the stimulator. The more the user becomes responsible for the selective operation of the various functions of the unit, the more active and alert such person will remain thereby diminishing the possible relaxing affects which could otherwise be obtained. Additionally, the confinement area alone may have adverse effects on occupants making them feel closed in or trapped and thus further raising anxiety levels.

SUMMARY OF THE INVENTION

This invention is directed to an enclosure in which one or more persons may be seated and entertained through the use of various sensory stimuli so as to relieve stress wherein the interior of the enclosure is made up of reflective surfaces which are angularly disposed relative to one another so as to cause multiple reflections of light patterns or images transmitted within the enclosure. The reflective surfaces are generally separated by a plurality of light emitting members with at least one surface providing a video screen panel permitting a varied display of light or video images to be transmitted into the enclosure and reflected by the inner surfaces thereof. Various sound and olfactory systems and stimuli are also provided within the controlled atmosphere of the enclosure and thereby combine with the visual elements to create an environment wherein the senses are completely stimulated to a heightened level in order to both entertain the occupants while simultaneously relieving stress.

It is the primary object of the present invention to provide an enclosure which may be used to entertain the occupants thereof through the use of integrated visual, audio and other sensory stimuli which together permit the occupants to experience a new environment in which the senses cause thought processes to be directed and focussed on the present activity within the enclosure and free of past or future worries or concerns.

It is another object of this invention to provide an apparatus which may be used by one or more persons in order to stimulate their various senses including the senses of hearing, seeing, depth perception, smell, taste, and body temperature in order to relax the person both mentally and physically and thereby reduce the harmful build up of personal stresses and anxieties.

It is another object of the present invention to provide an enclosure wherein a person may be seated and wherein the interior of the enclosure is mirrored in such a manner as to cause light waves to be reflected a plurality of times back to the person thereby creating an illusion of space and depth even within a small enclosure, and wherein various light patterns and/or video displays including pictures, movies and the like, may be introduced into the reflective area of the enclosure to thereby cause multiple lighting and color effects to stimulate the visual sensory perception of the individual.

It is a further object of the invention to provide a means for enabling a person to relieve both mental and physical stress by placing them within an environment which so stimulated their primary senses in a unified or integrated manner that total concentration on any one sense is generally alleviated so as to thereby relieve mental anxieties and pressures which are caused by conscious mental focusing on particular problems.

It is still a further object of the present invention to provide an enclosure for regulating the atmospheric environment which surrounds a person so as to place such person in a relaxed and comfortable condition while simultaneously creating illusions of depth and space both in visual and audio terms in an effort to make the physical body feel at ease as if adrift in a protected space so that physical stress is relieved through relaxation of the body muscular system.

BRIEF DESCRIPTION OF THE DRAWINGS

FIG. 3 is a side elevational view taken from the left side of the enclosure shown in FIG. 1.

FIG. 4 is a partial cross-sectional view taken along the lines 4—4 of FIG. 2.

FIG. 5 is a fragmented cross-sectional view taken along lines 5—5 of FIG. 1 showing the mirrored floor panel of the present invention.

FIG. 6 is a cross-sectional view taken along lines 6—6 of FIG. 3 showing the cross section of the mirrored panel members, the frame connection members, and the light piping between each of the panel members.

FIG. 7 is a cross-sectional view of another embodiment of the invention showing an alternative panel, frame and fiber optic display construction as taken along the lines of 6—6 in FIG. 3.

FIG. 8 is a cross-sectional view taken along lines 8—8 of FIG. 7.

FIG. 9 is a cross-sectional view taken through the base of the enclosure of the present invention showing the various sensory stimulating and environment control apparatus incorporated therein.

FIG. 10 is a sectional view taken along lines 10—10 of FIG. 9.

DESCRIPTION OF THE PREFERRED EMBODIMENT

Figure 1:
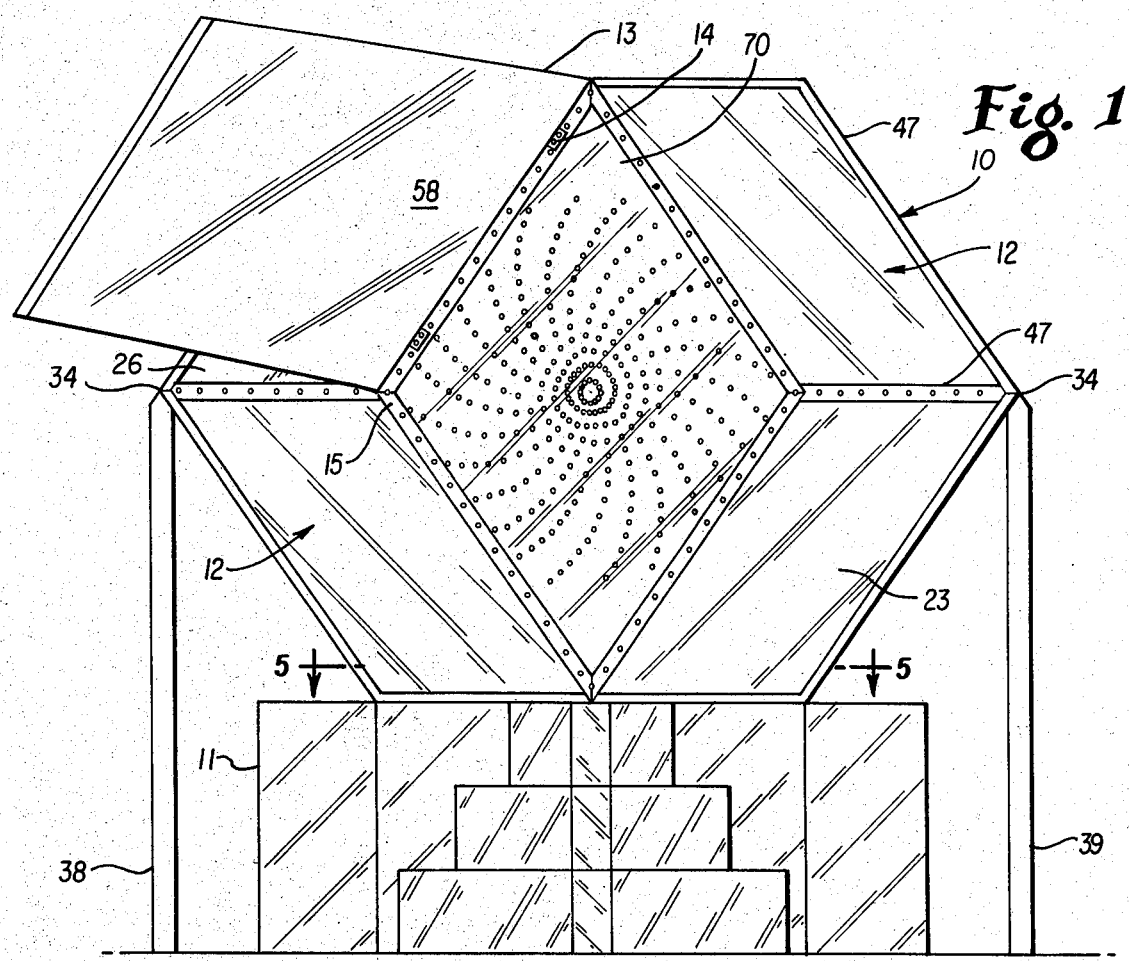
FIG. 1 is a front elevational view of a preferred form of the invention showing the sensory stimulation enclosure in the shape of a rhombic dodecahedron.
Figure 2:
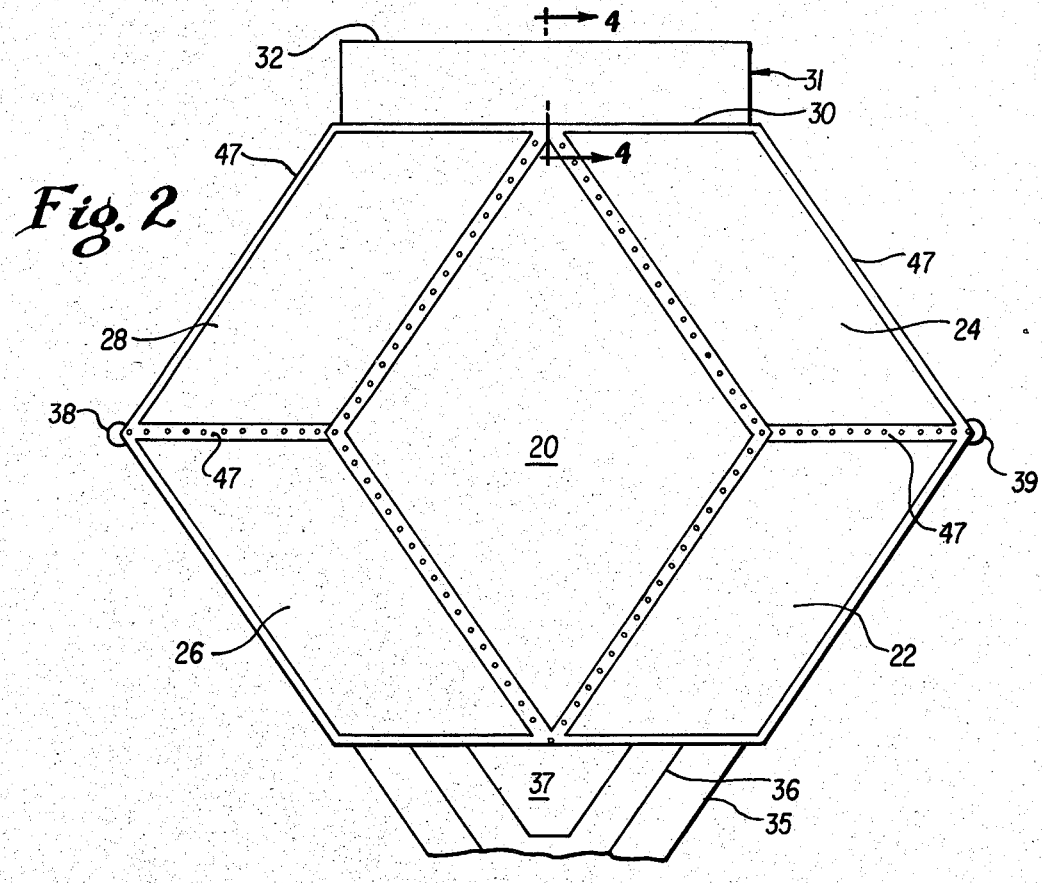
FIG. 2 is a top plan view of the enclosure of FIG. 1.

With continued reference to the drawings and particular reference to FIGS. 1 through 3, the sensory stimulation and entertainment enclosure 10 of the present invention is shown as being mounted to an enlarged base portion 11. The enclosure is shown as being a twelve sided geometric shape or rhombic dodecahedron consisting of separate panels which are joined in edge-to-edge relationship and which are generally in the shape of a parallelogram.

The front of the enclosure is formed by a door 13 which is hingedly mounted at 14 to a framework 15 which defines an open passageway 16 into the enclosure. Due to the twelve side configuration of the enclosure, the upper wall 20 extends generally parallel to the floor panel 21. The right sidewalls include panels 22 through 25 respectively with panels 22 and 23 being oriented in upper and lower relationship, respectively, adjacent the passageway 16 into the enclosure. The left sidewalls are constructed of angularly related panels 26 through 29 with panel members 26 and 27 being oriented in upper and lower relationship, respectively, adjacent the passageway 16. The door 13 and each of the top and side panels 20 and 22 through 29 are generally formed in a similar fashion and are the same shape. The bottom panel 21 and rear portion 30 of the enclosure are generally in the same parallelogram shape as the remaining panels, however, they are structured somewhat differently. The rear portion 30 of the enclosure is covered by a housing 31 having an exterior shape coinciding with the shape of the remaining panels. The housing, however, extends outwardly from the geometric configuration of the enclosure, as shown in FIG. 2, to an end wall 32 thereof. The rear housing 31 is attached by hinges 33 to panels 24 and 25 and is thereby openable and moveable with respect to the adjacent panel members of the enclosure. An appropriate latch (not shown) may also be provided to secure the housing with respect to the panel members.

As previously mentioned, the sensory stimulation and entertainment enclosure 10 is mounted to a base 11 which is elevated in order to contain a plurality of electrical components as will hereinafter be described in greater detail. Entry through the passageway 16 into the enclosure is made via a plurality of generally triangularly oriented steps 35 through 37 which are provided adjacent the passageway and which abut one edge of the base. Due to the configuration of the preferred embodiment, it may be necessary to provide vertical support braces 38 and 39 which extend from a support surface upwardly to an apex 34 defined by each of the four sidewall panels on the left and right side of the enclosure.

The frame members and the panel members are shown in cross section in FIGS. 6 through 8. FIG. 6 shows the structure of the preferred embodiment while FIGS. 7 and 8 disclose an alternative embodiment for the panel and framing structure. All the panel members 20 through 29 have both interior and exterior mirrored surfaces 40 and 41, respectively. In FIG. 6, the mirrored surfaces 40 and 41 of panels 20 and 22 through 29 are shown as being mounted to wooden framing members 42. The edge framing members 42' are shaped so as to abut with members 42' of an adjacent panel and are secured in abutting relationship by steel connector members 43 which are suitably fastened thereto by means such as screws 44. If desired, the open spaces 45 between the interior and exterior panels may be filled with a solid foam material (not shown) in order to give a continuous support to the mirrored surfaces throughout the entire panel as well as to further insulate the interior of the enclosure from exterior sound sources.

Both the interior and exterior joints between the panel members are covered with molding strips 46 and 47, respectively. The molding strips are generally U-shaped in cross section so as to define passageways 48 and 49 between the strips and the panel joints. The ends of each molding strip are mitered so as to properly align with the ends of other strips, as shown in FIG. 3.

A plurality of spaced openings 50 are provided through the exterior molding strips 47 so as to receive the ends of a first bundle of fiber optic elements 52. Similarly, a plurality of spaced openings 52 are provided along the length of the interior molding strips 46. The ends of a second bundle of fiber optic elements 66 are received within the openings 53. In order to illuminate the openings 50 and 53, light will be conducted through the first and second fiber optic bundle of elements. In this manner, the openings both interiorly and exteriorly of the enclosure with be illuminated for purposes which will be described in greater detail hereinafter.

The floor panel 21 is constructed having an interior mirrored surface 56 which is reinforced and mounted to a core material such as ½ inch to ¼ inch plywood 57. The continuous engagement between the mirrored surface and the core material will give the surface added strength and prevent the same from breaking during normal use of the enclosure. The structure of door panel 13 will be generally the same as that for panel members 20 and 22 through 29 except that additional framing may be required. The mirrored interior surface 58 is shown in FIG. 1.

As a alternate embodiment of the invention, the panels may be fabricated and joined as shown in FIGS. 7 and 8. In this embodiment, each of the panel members may be joined along its edge portions by a tubular frame structure consisting of a plurality of elongated tubes 60. Each of the tubes 60 has an upper and lower outer flange portion 61 and 62 which extend generally flush with the outer mirrored surface 41 of the panel members. The end portions 64 of the panel members are arcuately shaped so as to cooperatively engage and abut the arcuate edge of the tubes 60. The panels and tubes may be secured by any number of fastening means including mechanical fasteners or may be adhesively secured in assembled relationship. A plurality of openings 65 and 66 are provided in spaced relationship through the sidewalls of each tube member so that the openings 65 are oriented outwardly of the enclosure while the openings 66 are oriented inwardly of the enclosure. In order to illuminate each of the openings in the tubular frame members, a plurality of fiber optic elements 67 are disposed within the tube members and the end portions 68 thereof are mounted within one of the openings 65 and 66. In this manner, every opening will have a fiber optic element inserted therein so that light can be conducted along the length of the tubular members both to the interior and exterior of the enclosure for purposes that will be described in greater detail hereinafter.

The structure of the panel members 20 and 22 through 29 may also be altered as shown in FIGS. 7 and 8. In this embodiment, the panel members include a generally solid core member 69 such as a ½ inch to ⅜ inch plywood over both sides of which are placed the mirrored surfaces 40 and 41.

As previously noted, the rear of the enclosure is structured differently than the remaining panel members. With particular respect to FIG. 4, the interior of the enclosure adjacent the rear portion thereof is closed by a rear mirrored video screen 70 which is mounted within flange members 71 which are secured to the frame members 42' extending between the panel members adjacent the rear of the enclosure. As previously discussed, the housing 31 is hingedly mounted to the frame members 42' so as to be in spaced and covering relationship with respect to the rear video screen 70. The housing is formed having a wooden core portion 72 which may be constructed of a ½ inch to ⅜ inch plywood or other material, and which is covered on its exterior by mirrored surfaces 73.

In addition to the panel members of the enclosure having exterior mirrored surfaces, the base portion 11 and the stairs 35 through 37 are also constructed so as to have exteriorly mirrored surfaces, as specifically shown in FIG. 1. In this manner, the entire exterior of the sensory stimulation enclosure, including its base, resemble a crystal-like element having a plurality of reflecting and light emitting surfaces which are used to create a perception of increased depth and size. As discussed earlier in the specification, some people have a fear of being confined in relatively small enclosures, however, the mirrored construction of the present invention will help in alleviating or calming such claustrophobic fears as the plurality of reflective wall surfaces will create an illusion of depth and distance in visual field and scope thereby expanding the apparent environment within the enclosure.

With particular reference to FIG. 5, the interior floor panel 21 is shown as it is mounted in relationship with the rear sidewall panels 23, 25, 27 and 29. In order to control the ambient air and flow of air through the enclosure, the floor panel 21 is mounted in an elevated position with respect to the base member so as to provide airflow openings 76 and 77 on opposite sides thereof. As shown by the arrows, the airflow is introduced through air inlet opening 76 and exhausted through outlet opening 77. With reference to FIG. 9, the flow of air is controlled by a blower element 80 which is mounted within the base 11 and which is also connected to temperature and/or thermostatic control elements 81 mounted in the base for controlling the temperature and humidity of the air within the enclosure. It is important that the ambient conditions within the enclosure are ideal in order to provide for the comfort and relaxation of a person therein. The senses should not be adversely affected by ambient air conditions which could either be too hot, too cool, too dry, or too moist. Appropriate control means which are conventionally available may be used to monitor and to alter the ambient conditions within the enclosure. As opposed to mounting the floor portion 21 is an elevated position with respect to the base to form the air inlet and outlet slots, the opposite edge portions of the panel member 21 may be cut or reduced in size to thereby form openings through which the air may be introduced and exhausted from the enclosure.

With particular reference to FIG. 9, the base 11 of the enclosure is shown in cross section. The base is formed having a support material 82 which may be a ½ inch to ⅜ inch plywood which is secured to frame elements 83. The frame element 83 supports the floor portion of the enclosure in the aforementioned elevated position to allow for the appropriate air flow. As previously mentioned, the exterior walls of the base member are covered with mirrors so that the base will be exteriorly reflective in coordination and conjunction with the remainder of the structure.

In order to stimulate the various senses of a person within the structure, a plurality of stimulus producing equipment are mounted within the base portion 11. As previously discussed, a plurality of fiber optics extend through the frame member moldings 46 and 47 and terminate at one end either into or outside of the enclosure. Each fiber optic bundle 52 and 55 extends through the molding network down into the base adjacent to the projectors 84 and color wheel assembly 85 which provide the light source for the fiber optic bundles. The light from the projectors 84 is focussed on the ends of the fiber optic bundles through the rotating color wheels 86 and a slotted disc or wheel 87. As shown, the overlapping relationship of the slotted disc and the color wheels will cause various light patterns and colors to be received by the ends of the fiber optic elements. The various light patterns which are focused on the ends of the fiber bundles 52 and 55 will create a variety in the light patterns which are displayed from the opposite ends thereof either interiorly or exteriorly of the enclosure.

To create additional visual stimulus within the enclosure, a fiber optic display may also be incorporated into the rear housing 31 of the enclosure. The rear panel optical display 90 is shown in FIG. 4 as including a plurality of fiber optics 91 which have one end portion thereof mounted through openings in a support matrix 92 so as to be retained in a specifically aligned and designated relationship with regard to one another. An example of a typical aligned relationship is shown by the pattern displayed through the rear wall or rear video screen 70 shown in FIG. 1. The other ends 93 of the fiber optic elements terminate adjacent to one side of a color wheel 94 which is rotated by a motor 95 and through which light from a light projector 96 is directed. Light emitted or projected onto the face of the fiber optic elements is conveyed to the ends thereof and projected through the rear screen video panel 70 into the interior of the enclosure.

Generally, a person sitting within the enclosure will be positioned so that their back faces the rear screen video and, therefore, such video is not directly viewable so that the light patterns and images there from are perceived by the individual within the enclosure after being reflected by the angled surfaces of the interior of the enclosure. The rotation of the color wheel will, therefore, create a moving or changing light effect within the enclosure with the angled wall portions causing the light to move or appear to move at accelerated rates or at slower rates depending upon the way the pattern is reflected by the mirrored surfaces. This light pattern combines with the light pattern coming through the side frame members and will give an illusion of movement in space. The light patterns move totally around the individual within the enclosure, constantly moving at different rates and changing colors at random and thereby stimulate and heighten the visual senses both through color, depth, movement, light intensity, and depth perceived by the individual within the enclosure. In addition to the fiber optics 91, a video projector (not shown) could also be used to direct patterns of light through the rear screen thereby forming various light images which move within the enclosure. Alternatively, video games or special video light shows, music videos, photographs or movies may also be projected through the rear video screen.

The visual effects created by the light transmitted through the rear screen of the enclosure may be changed or altered by providing insertable matrix members 92 having varying forms or shapes and designs of fiber optics mounted thereto. The interchange of such support matrices may be accomplished by simply swinging the rear panel housing 31 about its pivoted engagement with the adjacent side panel members of the enclosure.

To further stimulate and entertain a person within the enclosure, other sensory affecting equipment is mounted within the base portion of the enclosure. Specifically, a sound system is incorporated in the base portion and includes a plurality of floor mounted speakers 97 which are connected to a conventional or holophonic type sound system 98 also mounted within the base. If desired, two or more speakers can be mounted within the interior of the enclosure adjacent corners formed between any pair of side panels so as to be generally oppositely directed with respect to one another.

Also incorporated in the base may be various conventional apparatus for releasing aromatic essences into the air flow to stimulate the olfactory senses of an occupant of the enclosure. To this end an aromatic dispenser 99 is provided adjacent the blower element 80 so that various aromas or fragrances may be selectively introduced into the air supply.

In the use of the sensory stimulation enclosure of the present invention, one or more people are seated on the mirrored floor within the enclosure preferably with their backs generally oriented toward the rear screen 70. Thereafter the swingable door 13 is closed against the frame members 15 defining the passage 16 into the enclosure. The area within the enclosure is totally mirrored with the exception of the moldings between panels. The fiber optics carried in the molding members are used to introduce various light patterns into the chamber. The color, pictorial or moving picture effects in the chamber are then initiated using the projection or color wheel system mounted in the rear portion of the enclosure. Due to the reflective inner surfaces and the angled relationship of the components, a sense of depth is obtained and the various light patterns move at varying rates within the enclosure. As the occupants of the enclosure are remote from the operating mechanisms and the control therefor, the light, sound and other sensory stimuli are introduced into the enclosure without any overt action being required on the part of those in the enclosure.

With the absence of outside activity and interruption and with the movement and ever changing images and patterns of the lights and sounds within the chamber, a person's thoughts will tend to follow the light through the endless reflections which are created and which give a feeling of space and nonconfinement. After short periods of time within the enclosure, the senses are so stimulated that stressful thoughts may be eliminated and all concentration falls on the present experience of the lights and sounds within the enclosure leaving past and future thoughts and concerns from the present awareness of the occupants. The lightness and endlessness which is simulated by the multiple reflected surfaces of the enclosure create a relaxing atmosphere so that the body stresses may also be relieved.

Although the preferred embodiment is disclosed as being in a geometric configuration of a rhombic dodecahedron, other geometric shapes could be used to obtain the same reflective effect within the enclosure.

I claim:

1. A sensory stimulation apparatus comprising an enclosure having a plurality of angularly related panel members and a door means, each of said panel members and said door means having inner and outer surface, each of said inner surfaces being mirrored, light emitting means mounted between each of said panel members adjacent said inner mirrored surfaces, means for movably mounting said door means, with respect to said panel members, a floor portion within said chamber, said floor portion having an inner mirrored surface, a housing mounted to said enclosure and extending outwardly with respect to said panel members, mounting means for moveably supporting said housing with respect to said panel members, first light projection means mounted within said housing so as to direct light through one of said panel members into said enclosure.

2. The sensory stimulation apparatus of claim 1 in which said enclosure is mounted to a base member, said light emitting means including a plurality of first fiber optic means which extend from one end within said base member to their other end within said enclosure and a second light projection means within said base member for projecting light onto said one end of said first fiber optic means.

3. The sensory stimulation apparatus of claim 2 in which said light emitting means includes first generally open channel means extending between each of said panel members along said inner mirrored surfaces, said first channel means defining substantially enclosed passageways, a plurality of spaced openings through said first channel means and oriented into said enclosure, said other ends of said first fiber optic means being mounted within said openings so as to direct light into said enclosure.

4. The sensory stimulation apparatus of claim 3 including air inlet and outlet openings in said enclosure adjacent said floor portion and air circulation means within said base member for moving air through said air inlet and outlet openings.

5. The sensory stimulation apparatus of claim 4 including temperature control means mounted within said base member for controlling the temperature of the air being circulated through said enclosure.

6. The sensory stimulation apparatus of claim 4 including sound means mounted within said base member for introducing sounds into said enclosure.

7. The sensory stimulation apparatus of claim 6 including olfactory stimulation means mounted within said base member.

8. The sensory stimulation apparatus of claim 3 in which said first light projection means includes a light source, a plurality of second fiber optic means mounted within said housing, a matrix support panel, means for removably mounting said matrix support panel adjacent said one of said panel members, a plurality of openings within said matrix support panel, said second fiber optic means having first and second ends, said first ends of said fiber optic means being mounted to receive light directed thereto by said light source and said second ends of said second fiber optic means being mounted within said openings of said matrix support panel so as to direct patterns of light through said one of said panel members into said enclosure.

9. The sensory stimulation apparatus of claim 8 including audio stimulation means mounted within said base member for conveying sound into said enclosure.

10. The sensory stimulation apparatus of claim 9 in which said first and second light projection means include means for changing the color of the light received by said second and said first fiber optic means respectively.

11. The sensory stimulation apparatus of claim 9 in which said outer surface of said door means and said panel members are mirrored, said housing having outer mirrored surfaces, and said base having outer mirrored surfaces.

12. The sensory stimulation apparatus of claim 11 including second channel means extending between each of said panel members along said outer mirrored surfaces defining substantially closed passageways, a plurality of spaced openings through said second channel means, third fiber optic means mounted within said second channel means and having a first end extending into said base member adjacent said second light projecting source and a second end mounted within said openings through said second channel means.

13. The sensory stimulation apparatus of claim 12 including steps for entering into said enclosure, said steps having exterior mirrored surfaces.

14. The sensory stimulation apparatus of claim 13 in which said enclosure is in the geometric shape of a rhombic dodecahedron.

15. The sensory stimulation apparatus of claim 12 in which said first and second channel means are integrally formed in a tubular member, said tubular member having first and second spaced and oppositely oriented openings therein in which said first and third fiber optic means are mounted, respectively, and said panel members being mounted to said tubular members.

16. A sensory stimulation apparatus comprising an enclosure defined by a plurality of panel members, each of said panel members having outer surfaces and interiorly mirrored surfaces, said panel members being joined in angular relationship with respect to one another so as to cause multiple reflections of light within said enclosure, at least one of said panel members including means adapted to permit light forms to be transmitted therethrough into the enclosure, and means for transmitting light forms through said one of said panel members and into said enclosure, and one of said panel members being movable with respect to the other of said panel members so as to provide access into said enclosure.

17. The sensory stimulation apparatus of claim 16 including molding means disposed between each of said panel members, a plurality of openings through said molding means, a plurality of light emitting members disposed within said openings and means for controlling the light emitted by said light emitting members.

* * * * *